(12) United States Patent
Branch et al.

(10) Patent No.: US 7,365,077 B2
(45) Date of Patent: Apr. 29, 2008

(54) PIPERAZINE BIS-AMIDE DERIVATIVES AND THEIR USE AS ANTAGONISTS OF THE OREXIN RECEPTOR

(75) Inventors: Clive Leslie Branch, Harlow (GB); Christopher Norbert Johnson, Harlow (GB); David John Nash, Harlow (GB); Geoffrey Stemp, Harlow (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 398 days.

(21) Appl. No.: 10/495,021

(22) PCT Filed: Nov. 6, 2002

(86) PCT No.: PCT/EP02/12476

§ 371 (c)(1),
(2), (4) Date: Oct. 15, 2004

(87) PCT Pub. No.: WO03/041711

PCT Pub. Date: May 22, 2003

(65) Prior Publication Data

US 2006/0252769 A1    Nov. 9, 2006

(30) Foreign Application Priority Data

Nov. 10, 2001 (GB) .................... 0127145

(51) Int. Cl.
A61K 31/496 (2006.01)
C07D 417/14 (2006.01)
C07D 401/12 (2006.01)
C07D 405/12 (2006.01)
C07D 405/14 (2006.01)

(52) U.S. Cl. ............... 514/253.06; 514/254.02; 514/254.09; 544/363; 544/369; 544/371; 544/373

(58) Field of Classification Search ............ None
See application file for complete search history.

(56) References Cited

U.S. PATENT DOCUMENTS

| | | | |
|---|---|---|---|
| 6,677,354 B2 | 1/2004 | Branch et al. .......... | 514/318 |
| 6,943,160 B2 | 9/2005 | Branch et al. .......... | 514/235.2 |
| 7,078,565 B2 | 7/2006 | Chan et al. ............. | 564/158 |
| 2004/0014315 A1 | 1/2004 | Lai et al. ............... | 438/680 |
| 2004/0180887 A1 | 9/2004 | Branch et al. .......... | 514/232.5 |
| 2004/0192673 A1 | 9/2004 | Gaillard et al. ........ | 514/217.04 |
| 2004/0215014 A1 | 10/2004 | Chan et al. ............. | 540/596 |
| 2006/0040937 A1 | 2/2006 | Branch et al. .......... | 514/235.5 |

FOREIGN PATENT DOCUMENTS

| WO | WO 01/96302 | 12/2001 |
|---|---|---|
| WO | WO 02/44172 | 6/2002 |
| WO | WO 03/032991 | 4/2003 |
| WO | WO 04/41791 | 5/2004 |
| WO | WO 04/41807 | 5/2004 |

OTHER PUBLICATIONS

Rodgers et al. Neuropeptides, vol.36(5), p. 303-325 (2002).*
Langmead et al. Br. J. Pharmacol., 141, p. 340-346 (2004).*
Cai et al. Expert Opin. Ther. Patents, vol. 16, p. 631-646 (2006).*
Database CA 'Online!Chemical Abstracts Service. "Hexahydroimidazo '1,5-a!pyrazines. I. Synthesis of 7-methyl-1,5,6,7,8,8a-hexahydroimidazo '1,5-a!pyrazin-3(2H)-one and derivatives". Database Accession No. 83:131550. XP002229197.
Patani et al. *Chem. Rev.*, 96: 3147-3176 (1996).

* cited by examiner

*Primary Examiner*—Emily Bernhardt
(74) *Attorney, Agent, or Firm*—Kathryn L. Sieburth; Mary E. McCarthy; Charles M. Kinzig

(57) ABSTRACT

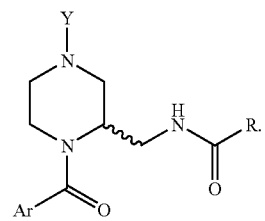

Disclosed are piperazine bis-amide derivatives useful as antagonists of the orexin receptor and pharmaceutical compositions containing the same.

22 Claims, No Drawings

PIPERAZINE BIS-AMIDE DERIVATIVES AND THEIR USE AS ANTAGONISTS OF THE OREXIN RECEPTOR

This application is a 371 of International Application No. PCT/EP02/12476 filed 6 Nov. 2002.

This invention relates to piperazine bis-amide derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. FHV, post-polio syndrome, and post-herpetic neuralgia; phantom limb pain; labour pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell*, 1998, 92, 573-585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides piperazine bis-amide derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders. These compounds may also be useful in the treatment of stroke, particularly ischaemic or haemorrhagic stroke. Additionally these compounds are useful in stroke, particularly ischemic or haemorrhagic stroke, and/or blocking the emetic response i.e. the compounds are useful in the treatment of nausea and vomiting.

International Patent Applications WO 99/09024, WO 99/58533, WO 00/47577 and WO 00/47580 disclose phenyl urea derivatives and WO 00/47576 discloses quinolinyl cinnamide derivatives as orexin receptor antagonists. WO01/96302 discloses N-aroyl cyclic amine derivatives and WO 02/44172 discloses morpholine derivatives as orexin receptor antagonists.

According to the invention there is provided compounds of formula (I):

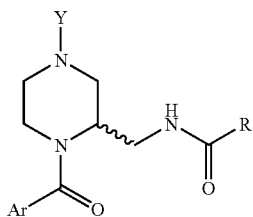

wherein:

Y represents hydrogen or $(C_{1-6})$ alkyl;

Ar represents an aryl group or a 5- or 6-membered heterocyclic ring containing up to 3 heteroatoms selected from N, O and S, wherein the aryl or heterocyclic group is substituted by $R^1$ and further optional substituents;

$R^1$ represents optionally substituted $(C_{1-6})$alkoxy, halo, optionally substituted $(C_{1-6})$alkyl, cyano, optionally substituted phenyl or an optionally substituted 5- or 6-membered heterocyclic ring containing up to 4 heteroatoms selected from N, O and S;

R represents an optionally substituted aryl or an optionally substituted heterocyclic ring system containing up to 4 heteroatoms selected from N, O and S;

or pharmaceutically acceptable derivatives thereof.

The term "aryl" includes single and fused rings, of which at least one is aromatic, which rings may be unsubstituted or substituted by, for example, up to three substituents as set out above. Each ring suitably has 5 or 6 ring atoms. When used herein in the definition of the Ar group, the term "aryl" includes phenyl or naphthyl. Suitably any aryl group, including phenyl, may be optionally substituted by up to five, preferably up to three substituents.

When used herein the term "heterocyclic" suitably includes, unless otherwise defined, aromatic and non-aromatic, single and fused, rings suitably containing up to four heteroatoms in each ring, each of which is selected from O, N and S, which rings, may be unsubstituted or substituted by, for example, up to three substituents. Each ring suitably has 5 or 6 ring atoms. A fused heterocyclic ring system may include carbocyclic rings and need include only one heterocyclic ring.

Preferably when $R^1$ represents an optionally substituted 5- or 6-membered heterocyclic ring it contains up to 3 heteroatoms selected from N, O and S.

Preferably when R represents an optionally substituted heterocyclic ring system it contains up to 3 heteroatoms selected from N, O and S.

Examples of 5- or 6-membered "heterocyclic" rings include furanyl, pyrrolyl, thienyl, oxazolyl, thiazolyl, imidazolyl, oxadiazolyl, thiadiazolyl, pyridinyl, triazolyl, triazinyl, pyridazyl, pyrimidinyl, isothiazolyl, isoxazolyl, pyrazinyl or pyrazolyl.

Examples of fused heterocyclic rings include quinoxalinyl, quinazolinyl, pyridopyrazinyl, benzoxazolyl, benzothiophenyl, benzimidazolyl, naphthridinyl, quinolinyl, benzofuranyl, indolinyl or isoquinolinyl.

Y is preferably hydrogen or methyl.

Preferably where Ar represents an optionally substituted phenyl ring or and optionally substituted 5- or 6-membered heterocyclic group containing up to 3 heteroatoms selected from N, O and S, the $R^1$ group is situated adjacent to the point of attachment to the amide carbonyl.

Ar preferably represents an optionally substituted phenyl, pyrazolyl or thiazolyl, more preferably thiazolyl.

Preferably $R^1$ represents an optionally substituted phenyl or furanyl, more preferably an optionally substituted phenyl.

Preferably, R is an optionally substituted 5- or 6-membered heterocyclic group containing up to 3 heteroatoms selected from N, O and S or an optionally substituted fused heterocyclic ring system.

Preferably R is an optionally substituted fused heterocyclic ring system.

More preferably R represents an optionally substituted benzofuranyl, quinolinyl or indolinyl, even more preferably R represents an optionally substituted benzofuranyl or quinolinyl.

Optional substituents for the groups Ar, R and $R^1$ include halogen, hydroxy, oxo, cyano, nitro, $(C_{1-6})$alkyl, $(C_{1-6})$alkoxy, aryl, halo$(C_{1-6})$alkyl, halo$(C_{1-6})$alkoxy, aryl$(C_{1-6})$alkoxy, $(C_{1-6})$alkylthio, hydroxy$(C_{1-6})$alkyl, $(C_{1-6})$alkoxy$(C_{1-6})$alkyl, $(C_{3-6})$cycloalkyl$(C_{1-6})$alkoxy, $(C_{1-6})$alkanoyl, $(C_{1-6})$alkoxycarbonyl, $(C_{1-6})$alkylsulfonyl, $(C_{1-6})$alkylsulfonyloxy, $(C_{1-6})$alkylsulfonyl$(C_{1-6})$alkyl, arylsulfonyl, arylsulfonyloxy, arylsulfonyl$(C_{1-6})$alkyl, $(C_{1-6})$alkylsulfonamido, $(C_{1-6})$alkylamido, $(C_{1-6})$alkylsulfonamido$(C_{1-6})$alkyl, $(C_{1-6})$alkylamido$(C_{1-6})$alkyl, arylsulfonamido, arylcarboxamido, arylsulfonamido$(C_{1-6})$alkyl, arylcarboxamido$(C_{1-6})$alkyl, aroyl, aroyl$(C_{1-6})$alkyl, or aryl$(C_{1-6})$alkanoyl group; a group $R^3R^4N-$, $R^3OCO(CH_2)_r$, $R^3CON(R^4)(CH_2)_r$, $R^3R^4NCO(CH_2)_r$, $R^3R^4NSO_2(CH_2)_r$ or $R^3SO_2NR^4(CH_2)_r$ where each of $R^3$ and $R^4$ independently represents a hydrogen atom or a $(C_{1-6})$alkyl group or where appropriate $R^3R^4$ forms part of a $(C_{3-6})$azacyloalkane or $(C_{3-6})$(2-oxo)azacycloalkane ring and r represents zero or an integer from 1 to 4. Additionally when the substituent is $R^3R^4N(CH_2)_n$— or $R^3R^4N(CH_2)nO$, $R^3$ with at least one $CH_2$ of the $(CH_2)_n$ portion of the group form a $(C_{3-6})$azacycloalkane and $R^4$ represents hydrogen, a $(C_{1-4})$alkyl group or with the nitrogen to which it is attached forms a second $(C_{3-6})$azacycloalkane fused to the first $(C_{3-6})$ azacycloalkane.

Preferably, substituents for Ar are selected from halogen or optionally substituted phenyl, optionally substituted $(C_{1-6})$alkyl or optionally substituted $(C_{1-6})$alkoxy.

Preferably, substituents for $R^1$ are selected from halogen or optionally substituted $(C_{1-6})$alkyl or optionally substituted $(C_{1-6})$alkoxy.

Preferably, substituents for R are selected from halogen or optionally substituted phenyl, optionally substituted $(C_{1-6})$alkyl or optionally substituted $(C_{1-6})$alkoxy.

More preferably R is optionally substituted by a halogen, or optionally substituted $(C_{1-6})$alkoxy.

The preferred substituent for Ar is methyl.

The preferred substituent for $R^1$ is fluorine.

The preferred substituents for R are selected from methoxy and fluorine.

Preferred compounds of the invention are selected from:

| Example | Name |
|---|---|
| 1 | (RS)-2-((Benzofuran-4-yl)carbonylaminomethyl)-1-((4-(5-(4-fluorophenyl)-2-methyl)thiazolyl)carbonyl)-4-methylpiperazine |
| 2 | Quinoline-8-carboxylic acid (1-{1-[5-(4-fluoro-phenyl)-2-methyl-thiazol-4-yl]-methanoyl}-4-methyl-piperazin-2-ylmethyl)-amide |
| 3 | 5-Methoxy-benzofuran-4-carboxylic acid (1-{1-[5-(4-fluoro-phenyl)-2-methyl-thiazol-4-yl]-methanoyl}-4-methyl-piperazin-2-ylmethyl)-amide |

-continued

| Example | Name |
|---|---|
| 4 | Benzofuran-4-carboxylic acid (1-{1-[5-(4-fluoro-phenyl)-2-methyl-thiazol-4-yl]-methanoyl}-piperazin-2-ylmethyl)-amide |
| 5 | Benzofuran-7-carboxylic acid (1-{1-[5-(4-fluoro-phenyl)-2-methyl-thiazol-4-yl]-methanoyl}-piperazin-2-ylmethyl)-amide |
| 6 | 5-Fluoro-benzofuran-7-carboxylic acid (1-{1-[5-(4-fluoro-phenyl)-2-methyl-thiazol-4-yl]-methanoyl}-piperazin-2-ylmethyl)-amide |
| 7 | Quinoline-8-carboxylic acid (1-{1-[5-(4-fluoro-phenyl)-2-methyl-thiazol-4-yl]-methanoyl}-piperazin-2-ylmethyl)-amide |
| 8 | 6-Methoxy-benzofuran-4-carboxylic acid (1-{1-[5-(4-fluoro-phenyl)-2-methyl-thiazol-4-yl]-methanoyl}-piperazin-2-ylmethyl)-amide |
| 9 | 7-Methoxy-benzofuran-4-carboxylic acid (1-{1-[5-(4-fluoro-phenyl)-2-methyl-thiazol-4-yl]-methanoyl}-piperazin-2-ylmethyl)-amide |
| 10 | 5-Methoxy-benzofuran-4-carboxylic acid (1-{1-[5-(4-fluoro-phenyl)-2-methyl-thiazol-4-yl]-methanoyl}-piperazin-2-ylmethyl)-amide |
| 11 | (S)-2-(((1-(6-Fluoro-2,3-dihydro-indol-1-yl)carbonyl)amino)methyl)-1-((4-(5-(4-fluorophenyl)-2-methyl)thiazolyl)carbonyl)-piperazine trifluoroacetate |
| 12 | (S)-2-(((1-(6-Fluoro-2,3-dihydro-indol-1-yl)carbonyl)amino)methyl)-1-((2-(2-furanyl)phenyl)carbonyl)-piperazine trifluoroacetate | and pharmaceutically acceptable derivatives thereof.

In the groups R and Ar, substituents positioned ortho to one another may be linked to form a ring.

When a halogen atom is present in the compound of formula (I) it may be fluorine, chlorine, bromine or iodine.

When the compound of formula (I) contains an alkyl group, whether alone or forming part of a larger group, e.g. alkoxy or alkylthio, the alkyl group may be straight chain, branched or cyclic, or combinations thereof, it is preferably methyl or ethyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject invention also includes isotopically-labeled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I.

Compounds of the present invention and pharmaceutically acceptable derivatives of said compounds that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^8$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula (I) and following of this invention can generally be prepared by carrying out the procedures disclosed in the Schemes and/or in the Examples below, by substituting a readily available isotopically labeled reagent for a non-isotopically labeled reagent.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolic or residue thereof.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and derivatives thereof. The following scheme details one of the synthetic routes to compounds of the invention.

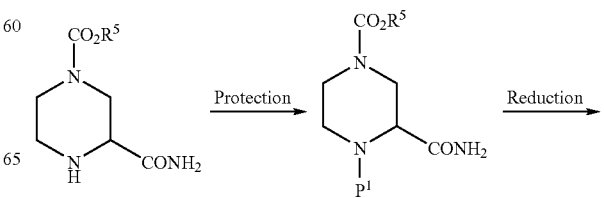

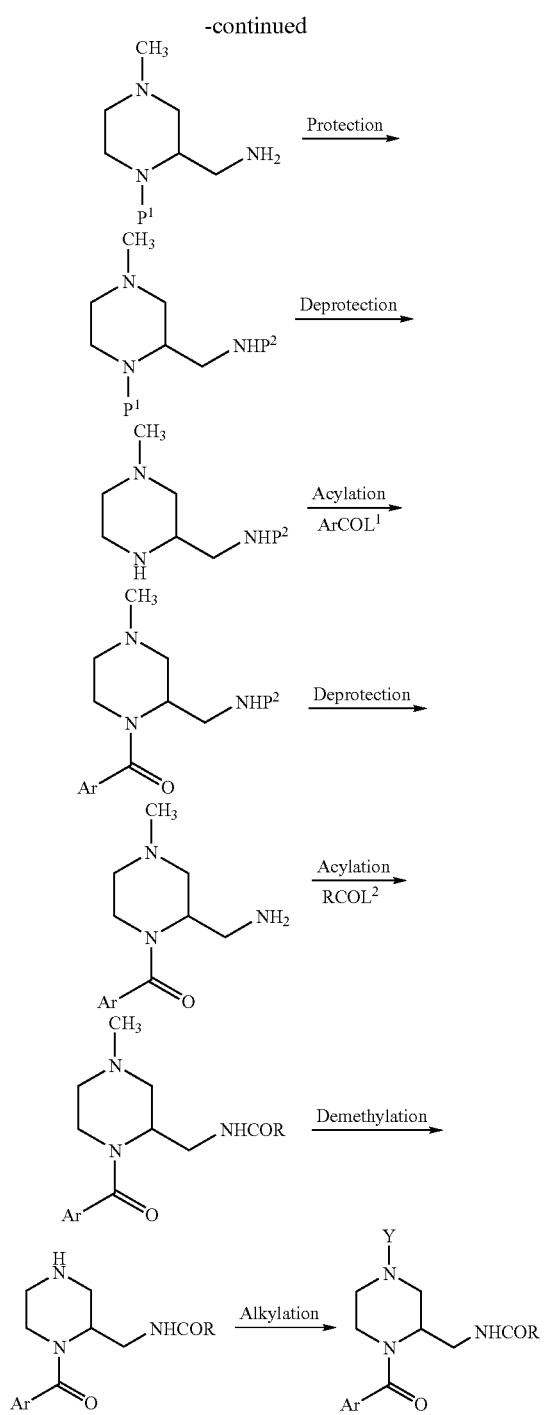

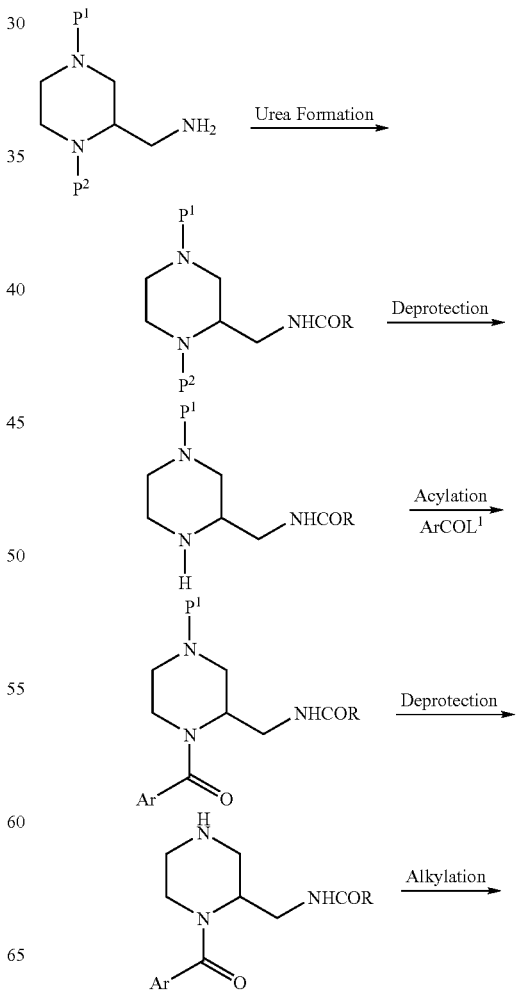

wherein Ar and R are as defined for compounds of formula (I), Y represents a $(C_{1-6})$alkyl, $R^5$ is an optionally substituted $(C_{1-6})$alkyl group, $P^1$ and $P^2$ are protecting groups and $L^1$ and $L^2$ are leaving groups.

Examples of protecting groups $P^1$ and $P^2$ include but are not restricted to t-butyloxycarbonyl, trifluoroacetyl, benzyloxycarbonyl and optionally substituted benzyl. Deprotection conditions will depend on the particular protecting group; for the groups mentioned above these are respectively, acid (e.g. trifluoroacetic acid in dichloromethane), base (e.g. potassium carbonate in a solvent such as aqueous methanol) and catalytic hydrogenolysis in an inert solvent (e.g. using palladium on charcoal in a lower alcohol or ethyl acetate).

Examples of suitable leaving groups $L^1$ and $L^2$ include halogen, hydroxy, OC(=O)alkyl, OC(=O)O-alkyl and $OSO_2Me$. Acylation may be carried out using a wide range of known conditions, e.g. in an inert solvent such as dichloromethane, in the presence of a base such as triethylamine. Alternatively these steps may be carried out when $L^1$ or $L^2$ represents hydroxy, in which case the reaction takes place in an inert solvent such as dichloromethane in the presence of a diimide reagent such as 1-ethyl-3-(3-dimethylaminopropyl)carbodiimide hydrochloride, and an activator such as 1-hydroxybenzotriazole.

Reduction of the amide can be carried out using known methods e.g. with a metal hydride reducing agent such as lithium aluminium hydride in an inert solvent such as diethyl ether or tetrahydrofuran.

Within scheme 1 the protecting groups $P^1$ and $P^2$ are chosen to be different and there is scope for functional group interchange and use of optional protecting groups within Ar, R $R^1$, and for example when Y is H, preferably a protecting group is used.

-continued

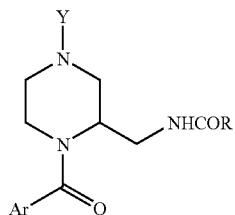

wherein Ar is as defined for formula (I), Y represents a (C$_{1-6}$) alkyl, R represents an optionally substituted heterocyclic ring system as defined for formula (I), P$^1$ and P$^2$ are protecting groups and L$^1$ is a leaving group as described for Scheme 1. Formation of the urea bond may be carried out using methods known to those skilled in the art. For example, in an inert solvent such as dichloromethane or dimethylformamide, by reaction with a carbamoyl chloride reagent either directly, or generated in situ from suitable amines with reagents such as phosgene or triphosgene. Alternatively this reaction may be carried out with a suitable amine in an inert solvent in the presence of dicarbonyl reagents such as 1,1'-carbonyldiimidazole.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable derivatives thereof.

Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human Orexin receptor is required such as obesity and diabetes; prolactinoma; hypoprolactinemia; hypothalamic disorders of growth hormone deficiency; idiopathic growth hormone deficiency; Cushing's syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; bulimia and hypopituitarism.

The compounds of formula (I) or pharmaceutically acceptable derivatives thereof are also useful in the treatment of stroke, particular ischaemic or haemorrhagic stroke. Furthermore the compounds of formula (I) or pharmaceutically acceptable derivatives useful in the blocking an emetic response.

The compounds of formula (I) and their pharmaceutically acceptable derivatives are particularly useful for the treatment of obesity, including obesity associated with Type 2 diabetes, and sleep disorders. Additionally the compounds are useful in stroke and/or blocking the emetic response i.e. nausea and vomiting. The compounds of formula (I) and pharmaceutically acceptable derivatives thereof are also useful in the treatment of stroke, particularly ischaemic or haemorrhagic stroke.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; postoperative pain; neuralgia; and tolerance to narcotics or withdrawal from narcotics.

The invention also provides a method of treating or preventing diseases or disorders where an antagonist of a human Orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human Orexin receptor is required.

The invention also provides the use of a compound of formula (I), or a pharmaceutically acceptable derivatives thereof, in the manufacture of a medicament for the treatment or prophylaxis of diseases or disorders where an antagonist of a human Orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human Orexin-A has the amino acid sequence:

```
pyroGlu Pro Leu Pro Asp Cys Cys Arg Gln Lys Thr
   1            5                      10

Cys Ser Cys Arg Leu Tyr Glu Leu Leu His Gly Ala
      15                        20

Gly Asn His Ala Ala Gly Ile Leu Thr Leu-NH2
      25                  30
```

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, *Drosophila* or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1-D11b illustrate the preparation of intermediates to compounds of the invention.

Description 1

(RS)-1-Benzyl-4-(tert-butyloxycarbonyl)-2-carbamoylpiperazine

A solution of (RS)-1-(tert-butyloxycarbonyl)-3-carbamoylpiperazine (ref Bruce et al. Syn. Comm. 1995, 2673-84) (25 g, 0.109 mol) and benzaldehyde (11.1 ml, 0.109 mol) in 1,2-dichloroethane (550 ml) was stirred at room temperature for 1.5 h. Sodium triacetoxyborohydride (34.7 g, 0.163 mol) was added in one portion and the resultant stirred for a further 18 h. Dichloromethane (400 ml) was added and the mixture washed with saturated sodium hydrogen carbonate (600 ml). The organic layer was dried ($Na_2SO_4$) and evaporated in vacuo. The residue was chromatographed on silica gel eluting with 10-70% ethyl acetate in hexane to afford the title compound as a colourless solid (32.4 g, 93%).

$^1$H NMR ($CDCl_3$) δ: 1.45 (9H, s), 2.15 (1H, dt), 2.75-3.15 (4H, m), 3.28 (1H, d, J=14 Hz), 3.85 (1H, broad d), 3.96 (1H, d, J=14 Hz), 4.15 (1H, broad m), 5.63 (1H, broad s), 6.70 (1H, broad s), 7.2-7.5 (5H, m).

Description 2

(RS)-2-Aminomethyl-1-benzyl-4-methylpiperazine

1M Lithium aluminium hydride in tetrahydrofuran (112 ml, 0.112 mol) was added dropwise to a stirred solution of (RS)-1-benzyl-4-(tert-butyloxycarbonyl)-2-carbamoylpiperazine (D1) (15 g, 0.047 mol) in anhydrous tetrahydrofuran (300 ml) at room temperature under argon. On complete addition the reaction mixture was stirred at room temperature for 0.5 h, then at reflux for a further 1.5 h. The mixture was cooled to room temperature and treated sequentially with water (19.5 ml), 2N sodium hydroxide (22.5 ml) and water (19.5 ml) dropwise. Sodium sulphate was added and the resultant stirred for 0.3 h, filtered and the filtrate evaporated in vacuo to give the title compound (10.3 g, 100%).

Mass spectrum (AP$^+$): Found 220 (ME). $C_{13}H_{21}N_3$ requires 219.

Description 3

(RS)-1-Benzyl-4-methyl-2-(trifluoroacetylaminomethyl)piperazine

Trifluoroacetic anhydride (8.05 ml, 0.057 mol) in anhydrous dichloromethane (10 ml) was added dropwise to a stirred solution of (RS)-2-aminomethyl-1-benzyl-4-methylpiperazine (D2) (10.3 g, 0.047 mol) and triethylamine (9.25 ml, 0.066 mol) in anhydrous dichloromethane (400 ml) at 0° C. under argon. The resultant was stirred at 0° C. for 1 h, then at room temperature for 18 h. The mixture was washed with saturated sodium hydrogen carbonate (400 ml) and the organic layer dried (Na$_2$SO$_4$) and evaporated in vacuo. The residue was chromatographed on silica gel eluting with 50% ethyl acetate in hexane, then 0-10% methanol in ethyl acetate to yield the title compound as a pale green gum (6.06 g, 41%).

Mass spectrum (AP$^+$): Found 316 (MH$^+$). $C_{15}H_{20}F_3N_3O$ requires 315.

Description 4

(RS)-4-Methyl-2-(trifluoroacetylaminomethyl)piperazine

A solution of (RS)-1-benzyl-4-methyl-2-(trifluoroacetylaminomethyl)piperazine (D3) (6.06 g, 0.0192 mol) in ethanol (300 ml) was hydrogenated at atmospheric pressure in the presence of 10% palladium on charcoal (6 g, 54% paste with water) for 18 h. The mixture was filtered through Kieselguhr and the filtrate evaporated in vacuo to furnish the title compound as a colourless gum (4.07 g, 94%).

Mass spectrum (AP$^+$): Found 226 (MH$^+$). $C_{81}H_4F_3N_3O$ requires 225.

Description 5

(RS)-1-((4-(5-(4-Fluorophenyl)-2-methyl)thiazolyl)carbonyl)-4-methyl-2-(trifluoroacetylaminomethyl)piperazine A solution of 5-(4-fluorophenyl)-2-methylthiazole-4-carbonyl chloride (2.27 g, 8.9 mmol) in dichloromethane (20 ml) was added dropwise with ice cooling to a stirred solution of (RS)-4-methyl-2-(trifluoroacetylaminomethyl)piperazine (D4) (2 g, 8.9 mmol) and triethylamine (3.71 ml, 26.6 mmol) in dichloromethane (80 ml). On complete addition, cooling was removed and the reaction mixture stirred at room temperature for 2.5 h, washed with saturated sodium hydrogen carbonate and the organic layer dried (Na$_2$SO$_4$) and evaporated in vacuo. The residue was chromatographed on silica gel eluting with 0-5% methanol in dichloromethane to afford the title compound as a colourless solid (3.5 g, 89%).

Mass spectrum (AP$^+$): Found 445 (MH$^+$). $C_{19}H_{20}F_4N_4O_2S$ requires 444.

Description 6

(RS)-2-Aminomethyl-1-((4-(5-(4-fluorophenyl)-2-methyl)thiazolyl)carbonyl)-4-methylpiperazine A mixture of (RS)-1-((4-(5-(4-fluorophenyl)-2-methyl)thiazolyl)carbonyl)-4-methyl-2-(trifluoroacetylaminomethyl)piperazine (D5) (3.65 g, 8.2 mmol) and potassium carbonate (6 g, 43.5 mmol) in methanol (300 ml) and water (100 ml) was heated at reflux for 1.5 h. The reaction mixture was cooled to room temperature, evaporated in vacuo and the residue partitioned between brine (500 ml) and dichloromethane (150 ml). The aqueous layer was extracted with dichloromethane (3×150 ml) and the combined organic extracts dried (Na$_2$SO$_4$) and evaporated in vacuo to afford the title compound as a pale green gum (2.18 g, 76%).

Mass spectrum (AP$^+$): Found 349 (MH$^+$). $C_{17}H_{21}FN_4OS$ requires 348.

Description 7(a)

(RS)-2-((Benzofuran-7-yl)carbonylaminomethyl)-1-((4-(5-(4-fluorophenyl)-2-methyl)thiazolyl)carbonyl)-4-methylpiperazine A mixture of (RS)-2-aminomethyl-1-((4-(5-(4-fluorophenyl)-2-methyl)thiazolyl)carbonyl)-4-methylpiperazine (D6) (0.29 g, 0.83 mmol), benzofuran-7-carboxylic acid (0.148 g, 0.91 mmol), 1-(3-dimethylaminopropyl)-3-ethylcarbodiimide hydrochloride (0.176 g, 0.91 mmol) and 1-hydroxybenzotriazole hydrate (0.02 g, 0.13 mmol) in dichloromethane (8 ml) was shaken for 18 hrs. The reaction mixture was washed with saturated sodium hydrogen carbonate (6 ml) and the organic layer added directly onto a 10 g pre-packed silica gel cartridge. Elution with 0-100% ethyl acetate in hexane, then 1-10% methanol in ethyl acetate afforded the title compound as a colourless amorphous solid (0.29 g, 71%).

Mass spectrum (Electrospray LC/MS): Found 493 (MH$^+$). $C_{26}H_{25}FN_4O_3S$ requires 492.

The following compounds were prepared in a similar manner to Description 7 (a)

7(b)

(RS)-2-((5-Fluorobenzofuran-7-yl)carbonylaminomethyl)-S-((4-(5-(4-fluorophenyl)-2-methyl)thiazolyl)carbonyl)-4-methylpiperazine Mass spectrum (Electrospray LC/MS): Found 511 (MH$^+$). $C_{26}H_{24}F_2N_4O_3S$ requires 510.

7(c)

(RS)-1-((4-(5-(4-Fluorophenyl)-2-methyl)thiazolyl)carbonyl)-2-((6-methoxybenzofuran-4-yl)carbonylaminomethyl)-4-methylpiperazine Mass spectrum (Electrospray LC/MS): Found 523 (MX>). $C_{27}H_{27}FN_4O_4S$ requires 522.

7(d)

(RS)-1-((4-(5-(4-Fluorophenyl)-2-methyl)thiazolyl)carbonyl)-2-((7-methoxybenzofuran-4-yl)carbonylaminomethyl)-4-methylpiperazine Mass spectrum (Electrospray LC/MS): Found 523 (MH$^+$). $C_{27}H_{27}FN_4O_4S$ requires 522.

2-Aminomethyl-1-(benzyloxycarbonyl)-4-(tert-butyloxycarbonyl)piperazine was synthesised from piperazine-2-carboxylic acid as described in PCT/US0017472 (WO 01/00214) except that 1-(benzyloxycarbonyl)-2-hydroxymethyl-4-(tert-butyloxycarbonyl)-piperazine was prepared as described below.

Description 8

(R)-1-(Benzyloxycarbonyl)-2-hydroxymethyl-4-(tert-butyloxycarbonyl)-piperazine

To (S)-1-(benzyloxycarbonyl)$_4$-(tert-butyloxycarbonyl)-piperazine-2-carboxylic acid (15.2 g, 0.04 mol) in tetrahydrofuran (200 ml) at 0° C. under argon was added borane (1M soln. in THF; 111 ml, 0.11 mol) dropwise over 15 min. The resulting mixture was stirred for 1 h, maintaining the temperature between 0° C. and 5° C., and then allowed to reach room temperature and stirred a further 18 h. The mixture was then carefully added, with stirring, to 5% g. acetic acid in water (1 l). After 1 h, the organics were evaporated in vacuo and the residual aqueous extracted with ethyl acetate (300 ml×4). The combined extracts were dried (Na$_2$SO$_4$), and evaporated in vacuo to a colourless oil. Chromatography on silica gel eluting with ethyl acetate-hexane mixtures afforded the title product (11 g, 75%) as a colourless oil.

Mass spectrum (AP$^+$): Found 351 (MH$^+$). $C_{18}H_{26}N_2O_5$ requires 350.

Description 9

(R)-1-(Benzyloxycarbonyl)-4-(tert-butyloxycarbonyl)-2-(((1-(6-fluoro-2,3-dihydro-indol-1-yl)carbonyl)amino)methyl)-piperazine (R)-2-Aminomethyl-1-(benzyloxycarbonyl)-4-(tert-butyloxycarbonyl)piperazine (0.4 g, 1.15 mmol) in dichloromethane (10 ml) was added dropwise under argon to a stirred solution of 1,1'-carbonyldiimidazole (0.186 g, 1.15 mmol) in dichloromethane (10 ml) at room temperature. After 1.5 h, the resulting mixture was evaporated in vacuo and to the residue in dimethylformamide (10 ml) was added 5-fluoroindoline (0.157 g, 1.15 mmol) and the reaction mixture heated at 100° C. for 5 h. After cooling to room temperature and stirring for 18 h, the reaction mixture was poured into water and extracted twice with ether. The combined extracts were dried and evaporated in vacuo and the residue chromatographed on silica gel, eluting with a 10% ethyl acetate/hexane to 2% methanol/ethyl acetate gradient to afford the title product (0.5 g, 85%). Mass spectrum (AP$^+$): Found 513 (MH$^+$). $C_{27}H_{33}FN_4O_5$ requires 512.

Description 10

(R)-1-(tert-Butyloxycarbonyl)-3-(((1-(6-fluoro-2,3-dihydro-indol-1-yl)carbonyl)amino)methyl)-piperazine The product of D9 (0.5 g, 0.98 mmol) in ethanol (15 ml) was hydrogenated at NTP over 10% Pd/C (0.2 g, 50% aq. paste) for 7.75 h, filtered through kieselguhr, washing with ethanol and the filtrate evaporated to afford the title compound (0.39 g, 100%) which was used without further purification. Mass spectrum (AP$^+$): Found 379 (MH$^+$). $C_{19}H_{27}FN_4O_3$ requires 378.

Description 11(a)

(R)-1-(tert-Butyloxycarbonyl)-3-(((1-(6-fluoro-2,3-dihydro-indol-1-yl)carbonyl)amino)methyl)-4-((4-(5-(4-fluorophenyl)-2-methyl)thiazolyl)carbonyl)piperazine 5-(4-Fluorophenyl)-2-methylthiazole-4-carbonyl chloride (0.044 g, 0.19 mmol) in dichloromethane (1 ml) was added to a solution of D10 (0.06 g, 0.16 mmol) and triethylamine (0.11 ml, 0.8 mmol) in dichloromethane (2 ml) and the mixture stirred for 18 h at room temperature. The reaction mixture was washed with saturated sodium hydrogen carbonate and the organic layer applied directly to a 10 g pre-packed silica gel cartridge and eluted with an ethyl acetate-hexane gradient to afford the title compound (0.075 g, 75%). Mass spectrum (AP$^+$): Found 598 (MH$^+$). $C_{30}H_{33}F_2N_5O_4S$ requires 597.

The following compound was prepared in a similar manner to Description 11(a).

11(b)

(R)-1-(tert-Butyloxycarbonyl)-3-(((1-(6-fluoro-2,3-dihydro-indol-1-yl)carbonyl)amino)methyl)-4-((2-(2-furanyl)phenyl)carbonyl)-piperazine Mass spectrum (AP$^+$): Found 549 (MH$^+$). $C_{30}H_{33}FN_4O_5$ requires 548.

EXAMPLE 1

(RS)-2-((Benzofuran-4-yl)carbonylaminomethyl)-1-((4-(5-(4-fluorophenyl)-2-methyl)thiazolyl)carbonyl)-4-methylpiperazine A mixture of (RS)-2-aminomethyl-1-((4-(5-(4-fluorophenyl)-2-methyl)thiazolyl)carbonyl)-4-methylpiperazine (D6) (0.348 g, 1 mmol), benzofuran-4-carboxylic acid (0.162 g, 1 mmol), 1-(3-dimethylaminopropyl)-3-ethylcarbodiimide hydrochloride (0.192 g, 1 mmol) and 1-hydroxybenzotriazole hydrate (0.02 g, 0.13 mmol) in dichloromethane (30 ml) was stirred for 18 h at room temperature. The reaction mixture was washed with saturated sodium hydrogen carbonate (30 ml) and the organic layer dried (Na$_2$SO$_4$) and evaporated in vacuo. The residue was chromatographed on silica gel eluting with 0-100% ethyl acetate in hexane, then 1-10% methanol in ethyl acetate to afford the title compound as a colourless amorphous solid (0.344 g, 70%). Mass spectrum (Electrospray LC/MS): Found 493 (MH$^+$). $C_{26}H_{25}FN_4O_3S$ requires 492.

The compounds of the Examples below were prepared from the appropriate amine and acid using a similar process to that described in Example 1.

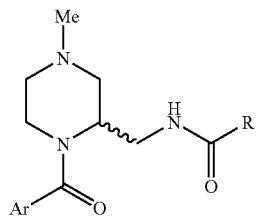

| Example | Ar | R | Mass Spectrum (Electrospray LC/MS) |
|---|---|---|---|
| 2 | 2-methyl-4-methyl-5-(4-fluorophenyl)thiazolyl | 8-methylquinolin-yl | Found MH$^+$: 504. $C_{27}H_{26}FN_5O_2S$ requires 503. |
| 3 | 2-methyl-4-methyl-5-(4-fluorophenyl)thiazolyl | 5-methoxy-4-methylbenzofuran-yl | Found MH$^+$: 523. $C_{27}H_{27}FN_4O_4S$ requires 522. |

EXAMPLE 4

(RS)-2-((Benzofuran-4-yl)carbonylaminomethyl)-1-((4-(5-(4-fluorophenyl)-2-methyl)thiazolyl)carbonyl) piperazine To a stirred solution of (RS)-2-((benzofuran-4-yl)carbonylaminomethyl)-1-((4-(5-(4-fluorophenyl)-2-methyl)thiazolyl)carbonyl)-4-methylpiperazine (product of Example 1) (0.35 g, 0.67 mmol) in 1,2-dichloromethane (6 ml) at 0° C. under argon was added 1-chloroethyl chloroformate (0.45 ml, 4.1 mmol) dropwise. The resultant mixture was stirred at 0° C. for 0.1 h, allowed to warm to room temperature over 0.5 h then heated at 65° C. for 20 h. The mixture was cooled to room temperature, diisopropylethylamine (2 ml) added and heated at gentle reflux for 1.5 h. On cooling, the mixture was evaporated in vacuo and the residue dissolved in methanol (10 ml) and heated at reflux for 2 h. The mixture was recooled, evaporated in vacuo and the residue partitioned between dichloromethane and saturated sodium hydrogen carbonate (100 ml of each). The aqueous layer was extracted with dichloromethane (100 ml) and the combined organics dried ($Na_2SO_4$) and evaporated in vacuo. The residue was chromatographed on silica gel eluting with 0-100% ethyl acetate in hexane, then 1-30% methanol in ethyl acetate to afford the title compound as a pale brown amorphous solid (0.135 g, 40%). Mass spectrum (Electrospray LC/MS): Found 479 (MH$^+$). $C_{25}H_{23}FN_4O_3S$ requires 478.

The racemic product of Example 4 was separated into its individual enantiomers using the following procedure. Racemate (135 mg) was dissolved in 20% v/v ethanol in n-hexane to a concentration of 5.0 mgml$^{-1}$. A 2 ml aliquot of this solution was applied to a Chiracel OD (250 mm×20 mm i.d.) chromatography column. Elution with 20% V/v ethanol in n-hexane at a flow rate of 17 mlmin$^{-1}$ using U.V. detection at 215 nm afforded the individual enantiomers. Repeat injection of 2 ml aliquots, pooling of relevant fractions and evaporation of the pooled fractions in vacuo afforded the following:

EXAMPLE (4a)

Faster Running Enantiomer (41 mg). Mass spectrum (AP$^+$): Found 479 (MH$^+$). $C_{25}H_{23}FN_4O_3S$ requires 478. Enantiomeric purity 98.8% e.e.

EXAMPLE (4b)

Slower Running Enantiomer (46 mg). Mass spectrum (AP$^+$): Found 479 (MH$^+$). $C_{25}H_{23}FN_4O_3S$ requires 478. Enantiomeric purity 94.0% e.e.

The compounds of the Examples below were prepared from the appropriate piperazine using a similar process to that described in Example 4.

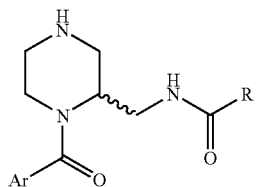

| Example | Ar | R | Mass Spectrum (Electrospray LC/MS) |
|---|---|---|---|
| 5 | 2-Me, 4-Me thiazole-5-yl-(4-fluorophenyl) | 7-methylbenzofuran-4-yl | Found MH$^+$: 479. $C_{25}H_{23}FN_4O_3S$ requires 478. |
| 6 | 2-Me, 4-Me thiazole-5-yl-(4-fluorophenyl) | 5-fluoro-7-methylbenzofuran-4-yl | Found MH$^+$: 497. $C_{25}H_{22}F_2N_4O_3S$ requires 496. |
| 7 | 2-Me, 4-Me thiazole-5-yl-(4-fluorophenyl) | 8-methylquinolin-5-yl | Found MH$^+$: 490. $C_{26}H_{24}FN_5O_2S$ requires 489. |
| 8 | 2-Me, 4-Me thiazole-5-yl-(4-fluorophenyl) | 6-methoxy-4-methylbenzofuran-? | Found MH$^+$: 509. $C_{26}H_{25}FN_4O_4S$ requires 508. |
| 9 | 2-Me, 4-Me thiazole-5-yl-(4-fluorophenyl) | 7-methoxy-4-methylbenzofuran-? | Found MH$^+$: 509. $C_{26}H_{25}FN_4O_4S$ requires 508. |
| 10 | 2-Me, 4-Me thiazole-5-yl-(4-fluorophenyl) | 6-methoxy-4-methylbenzofuran-? | Found MH$^+$: 509. $C_{26}H_{25}FN_4O_4S$ requires 508. |

EXAMPLE 11

(S)-2-(((1-(6-Fluoro-2,3-dihydro-indol-1-yl)carbonyl)amino)methyl)-1-((4-(5-(4-fluorophenyl)-2-methyl)thiazolyl)carbonyl)-piperazine trifluoroacetate To a solution of $D_{11}(a)$ (0.075 g, 0.13 mmol) in dichloromethane (10 ml) was added trifluoroacetic acid (2 ml) at room temperature. After 3 h, the reaction mixture was evaporated to afford the title product (0.08 g, 99%).

Mass spectrum (Electrospray LC/MS): Found 498 (MH$^+$). $C_{25}H_{25}F_2N_5O_2S$ require 497.

EXAMPLE 12

(S)-2-(((1-(6-Fluoro-2,3-dihydro-indol-1-yl)carbonyl)amino)methyl)-1-((2-(2-furanyl)phenyl)carbonyl)-piperazine trifluoroacetate The title compound (0.029 g, 88%) was prepared from D11 (b) using the method of Example 11.

Mass spectrum (Electrospray LC/MS): Found 449 (MH$^+$). $C_{25}H_{25}FN_4O_3$ requires 448.

It is understood that the present invention covers all combinations of particular and preferred groups described herein above.

Determination of Orexin-1 Receptor Antagonist Activity

The orexin-1 receptor antagonist activity of the compounds of formula (I) was determined in accordance with the following experimental method.

Experimental Method

CHO-DG44 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 Pd/well into 96-well black clear bottom sterile plates from Costar which had been pre-coated with 10 μg/well of poly-L-lysine from SIGMA. The seeded plates were incubated overnight at 37° C. in 5% CO$_2$.

Agonists were prepared as 1 mM stocks in water:DMSO (1:1). EC$_{50}$ values (the concentration required to produce 50% maximal response) were estimated using 1× half log unit dilutions (Biomek 2000, Beckman) in Tyrode's buffer containing probenecid (10 mM HEPES with 145 mM NaCl, 10 mM glucose, 2.5 mM KCl, 1.5 mM CaCl$_2$, 1.2 mM MgCl$_2$ and 2.5 mM probenecid; pH7.4). Antagonists were prepared as 10 mM stocks in DMSO (100%). Antagonist IC$_{50}$ values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 60 min at 37° C. in 5% CO$_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37° C. in 5% CO$_2$ for 30 minutes. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 seconds (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, TiPS, 1995, 16, 413-417) to generate a concentration effect value. Antagonist Kb values were calculated using the equation:

$$Kb = IC_{50}/(1+([3/EC_{50}]))$$

where EC$_{50}$ was the potency of human orexin-A determined in the assay (in nM terms) and IC$_{50}$ is expressed in molar terms.

Compounds of Examples tested according to this method had pKb values in the range 7.0 to 8.7 at the human cloned orexin-1 receptor.

The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37° C. in 5% CO$_2$.

Agonists were prepared as 1 mM stocks in water:DMSO (1:1). EC$_{50}$ values (the concentration required to produce 50% maximal response) were estimated using 1× half log unit dilutions (Biomek 2000, Beckman) in Tyrode's buffer containing probenecid (10 mM HEPES with 145 mM NaCl, 10 mM glucose, 2.5 mM KCl, 1.5 mM CaCl$_2$, 1.2 mM MgCl$_2$ and 2.5 mM probenecid; pH7.4). Antagonists were prepared as 10 mM stocks in DMSO (100%). Antagonist IC$_{50}$ values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 60 min at 37C in 5% CO$_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37C in 5% CO$_2$ for 30 min. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, *TiPS*, 1995, 16, 413-417) to generate a concentration effect value. Antagonist Kb values were calculated using the equation:

$$Kb = IC_{50}/(1+([3/EC_{50}])$$

where $EC_{50}$ was the potency of human orexin-A determined in the assay (in nM terms) and $IC_{50}$ is expressed in molar terms.

Compounds of Examples tested according to this method had pKb values in the range <6.5 to 7.0 at the human cloned orexin-2 receptor.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

Ar represents a phenyl, pyrazolyl or thiazolyl group, wherein the phenyl, pyrazolyl or thiazolyl group is substituted by $R^1$ and is further optionally substituted;

$R^1$ represents optionally substituted $(C_{1-6})$alkoxy, halo, optionally substituted$(C_{1-6})$alkyl, optionally substituted furanyl cyano, or optionally substituted phenyl;

R represents an optionally substituted naphthyl, quinolinyl, benzofuranyl or indolinyl group;

wherein the optional substituents for said optionally substituted $(C_{1-6})$alkoxy, $(C_{1-6})$alkyl, furanyl pyrazolyl, thiazolyl, quinolinyl, benzofuranyl, indolinyl, naphthyl and phenyl are selected from halogen, hydroxy, oxo, cyano, nitro, $(C_{1-6})$alkyl, $(C_{1-6})$alkoxy, aryl, halo$(C_{1-6})$alkyl, halo$(C_{1-6})$alkoxy, aryl$(C_{1-6})$alkoxy, $(C_{1-6})$alkylthio, hydroxy$(C_{1-6})$alkyl, $(C_{1-6})$alkoxy$(C_{1-6})$alkyl, $(C_{3-6})$cycloalkyl$(C_{1-6})$alkoxy, $(C_{1-6})$alkanoyl, $(C_{1-6})$alkoxycarbonyl, $(C_{1-6})$alkylsulfonyl, $(C_{1-6})$alkylsulfonyloxy, $(C_{1-6})$alkylsulfonyl$(C_{1-6})$alkyl, arylsulfonyl, arylsulfonyloxy, arylsulfonyl$(C_{1-6})$alkyl, $(C_{1-6})$alkylsulfonamido, $(C_{1-6})$alkylamido, $(C_{1-6})$alkylsulfonamido$(C_{1-6})$alkyl, $(C_{1-6})$alkyl amido$(C_{1-6})$alkyl, arylsulfonamido, arylcarboxamido, arylsulfonamido$(C_{1-6})$alkyl, arylcarboxamido$(C_{1-6})$alkyl, aroyl, aroyl$(C_{1-6})$alkyl, aryl$(C_{1-6})$alkanoyl, $R^3R^4N-$, $R^3OCO(CH_2)_r$, $R^3CON(R^4)$ $(CH_2)_r$, $R^3R^4NCO(CH_2)_r$, $R^3R^4NSO_2(CH_2)_r$, and $R^3SO_2NR^4(CH_2)_r$, wherein each of $R^3$ and $R^4$ independently represents a hydrogen

---

---

The invention claimed is:

1. A compound of formula (I)

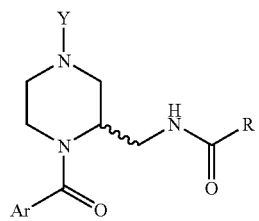

wherein:

Y represents hydrogen or $(C_{1-6})$ alkyl;

atom or a $(C_{1-6})$alkyl group or $R^3R^4$ forms part of a $(C_{3-6})$azacyloalkane or $(C_{3-6})$(2-oxo)azacycloalkane ring and r represents zero or an integer from 1 to 4;

or a pharmaceutically acceptable salt thereof.

2. A compound according to claim 1, wherein Y is hydrogen or methyl.

3. A compound as claimed in claim 1, wherein Ar represents an optionally substituted phenyl or thiazolyl group.

4. A compound according to claim 1, wherein the optional substituents for the Ar phenyl, pyrazolyl or thiazolyl group are selected from halogen, optionally substituted phenyl, optionally substituted $(C_{1-6})$alkyl and optionally substituted $(C_{1-6})$alkoxy.

5. A compound according to claim 3, wherein the optional substituents for the Ar phenyl or thiazolyl group are selected from halogen, optionally substituted phenyl, optionally substituted $(C_{1-6})$alkyl and optionally substituted $(C_{1-6})$alkoxy.

6. A compound according to claim 1, wherein the Ar phenyl, pyrazolyl or thiazolyl group is optionally substituted by methyl.

7. A compound according to claim 3, wherein the Ar phenyl or thiazolyl group is optionally substituted by methyl.

8. A compound according to claim 1, wherein $R^1$ represents an optionally substituted phenyl or furanyl group.

9. A compound according to claim 1, wherein $R^1$ represents an optionally substituted phenyl group.

10. A compound according to claim 8, wherein the optional substituents for said optionally substituted $R^1$ phenyl or furanyl group are selected from halogen, optionally substituted $(C_{1-6})$alkyl and optionally substituted $(C_{1-6})$alkoxy.

11. A compound according to claim 9, wherein the optional substituents for said optionally substituted $R^1$ phenyl group are selected from halogen, optionally substituted $(C_{1-6})$alkyl and optionally substituted $(C_{1-6})$alkoxy.

12. A compound according to claim 9, wherein said optionally substituted $R^1$ phenyl group is optionally substituted by fluorine.

13. A compound according to claim 1, wherein R represents an optionally substituted quinolinyl, benzofuranyl or indolinyl.

14. A compound according to claim 1, wherein the optional substituents for the R naphthyl, quinolinyl, benzofuranyl or indolinyl group are selected from halogen and optionally substituted $(C_{1-6})$alkoxy.

15. A compound according to claim 13, wherein the optional substituents for the R quinolinyl, benzofuranyl or indolinyl group are selected from methoxy and fluorine.

16. A compound selected from the group:
(RS)-2-((benzofuran-4-yl)carbonylaminomethyl)-1-((4-(5-(4-fluorophenyl)-2-methyl)thiazolyl)carbonyl)-4-methylpiperazine;
quinoline-8-carboxylic acid (1-{1-[5-(4-fluoro-phenyl)-2-methyl-thiazol-4-yl]-methanoyl}-4-methyl-piperazin-2-ylmethyl )-amide;
5-methoxy-benzofuran-4-carboxylic acid (1-{1-[5-(4-fluoro-phenyl)-2-methyl -thiazol-4-yl]-methanoyl}-4-methyl-piperazin-2-ylmethyl)-amide;
benzofuran-4-carboxylic acid (1-{1-[5-(4-fluoro-phenyl)-2-methyl-thiazol-4-yl]-methanoyl}-piperazin-2-ylm-ethyl)-amide;
benzofuran-7-carboxylic acid (1 -{1-[5-(4-fluoro-phenyl)-2-methyl-thiazol-4-yl]-methanoyl}-piperazin-2-ylmethyl)-amide;
5-fluoro-benzofuran-7-carboxylic acid (1-{1-[5-(4-fluoro-phenyl)-2-methyl-thiazol-4-yl]-methanoyl}-piperazin-2-ylmethyl)-amide;
quinoline-8-carboxylic acid (1-{1-[5-(4-fluoro-phenyl)-2-methyl-thiazol-4-yl]-methanoyl}-piperazin-2-ylm-ethyl)-amide;
6-methoxy-benzofuran-4-carboxylic acid (1-{1-[5-(4-fluoro-phenyl)-2-methyl -thiazol-4-yl]-methanoyl}-piperazin-2-ylmethyl)-amide;
7-methoxy-benzofuran-4-carboxylic acid (1-{1-[5-(4-fluoro-phenyl)-2-methyl-thiazol -4-yl]1-methanoyl}-piperzin-2-ylmethyl)-amide;
5-methoxy-benzofuran-4-carboxylic acid (1-{1-[5-(4-fluoro-phenyl)-2-methyl -thiazol-4-yl]-methanoyl}-piperzin-2-ylmethyl)-amide;
(S)-2-(((1-(6-fluoro-2,3-dihydro-indol-1-yl)carbonyl) amino)methyl)-1-((4-(5-(4-fluorophenyl)-2-methyl) thiazolyl)carbonyl)-piperazine trifluoroacetate;
(S)-2-(((1-(6-fluoro-2,3-dihydro-indol-1-yl)carbonyl) amino)methyl)-1-((2-(2-furanyl)phenyl)carbonyl)-piperazine trifluoroacetate;
or a pharmaceutically acceptable salt of any one thereof.

17. A pharmaceutical composition comprising the compound according to claim 1, or a pharmaceutically acceptable salt thereof, and a pharmaceutically acceptable carrier.

18. A pharmaceutical composition comprising the compound according to claim 3, or a pharmaceutically acceptable salt thereof, and a pharmaceutically acceptable carrier.

19. A method of treating a disease or disorder where an antagonist of a human orexin receptor is required, which comprises administering to a subject in need thereof an effective amount of the compound according to claim 1, or a pharmaceutically acceptable salt thereof, wherein said disease or disorder is selected from obesity, obesity observed in Type 2 diabetes, and a sleep disorder, where the sleep disorder is selected from insomnia and jet-lag syndrome.

20. A method of treating a disease or disorder where an antagonist of a human orexin receptor is required, which comprises administering to a subject in need thereof an effective amount of the compound according to claim 3, or a pharmaceutically acceptable salt thereof, wherein said disease or disorder is selected from obesity, obesity observed in Type 2 diabetes, and a sleep disorder, where the sleep disorder is selected from insomnia and jet-lag syndrome.

21. A method of treating insomnia comprising administering to a subject in need thereof an effective amount of the compound according to claim 1, or a pharmaceutically acceptable salt thereof.

22. A method of treating insomnia comprising administering to a subject in need thereof an effective amount of the compound according to claim 3, or a pharmaceutically acceptable salt thereof.

* * * * *

SEQUENCE LISTING

<160> NUMBER OF SEQ ID NOS: 1

<210> SEQ ID NO 1
<211> LENGTH: 35
<212> TYPE: PRT
<213> ORGANISM: Homo sapien

<400> SEQUENCE: 1

Glu Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu Asn His
        35